(12) United States Patent
Green

(10) Patent No.: US 12,048,422 B2
(45) Date of Patent: Jul. 30, 2024

(54) URINE SPECIMEN COLLECTION APPARATUS

(71) Applicant: Cynthia A. Green, Philadelphia, PA (US)

(72) Inventor: Cynthia A. Green, Philadelphia, PA (US)

(*) Notice: Subject to any disclaimer, the term of this patent is extended or adjusted under 35 U.S.C. 154(b) by 401 days.

(21) Appl. No.: 16/872,488

(22) Filed: May 12, 2020

(65) Prior Publication Data

US 2021/0353264 A1 Nov. 18, 2021

(51) Int. Cl.
*A61B 10/00* (2006.01)

(52) U.S. Cl.
CPC .... *A61B 10/007* (2013.01); *A61B 2010/0074* (2013.01); *A61B 2560/0431* (2013.01)

(58) Field of Classification Search
CPC ..... A61B 5/00; A61B 10/0045; A61B 10/007; A61B 10/00; A61B 5/20; A61B 2560/0431; A61B 2010/0074; B01L 3/00; B01L 3/50; B01L 3/508; G01N 33/48; A01K 23/005; A47G 23/0216
See application file for complete search history.

(56) References Cited

U.S. PATENT DOCUMENTS

| | | | |
|---|---|---|---|
| D290,880 S | 7/1987 | Blanton | |
| 4,832,046 A | 5/1989 | Parrish | |
| 5,147,342 A * | 9/1992 | Kane | A61B 10/0045 220/737 |
| 5,202,094 A * | 4/1993 | Jones | A47G 23/0216 D24/227 |
| D340,518 S | 10/1993 | Stahmer, Jr. et al. | |
| 5,422,076 A | 6/1995 | Jones | |
| D409,747 S | 5/1999 | Aiken | |
| 7,000,963 B2 | 2/2006 | Dodd | |
| 7,128,352 B1 * | 10/2006 | Phippen | A01K 23/005 294/1.5 |
| D567,368 S | 4/2008 | Guptill | |
| D607,995 S | 1/2010 | Miller | |
| 8,091,848 B1 * | 1/2012 | Reed | A61B 10/007 248/312 |
| 8,465,440 B1 * | 6/2013 | Grayson | A61B 10/007 D24/227 |
| 2002/0179794 A1 | 12/2002 | Yang | |
| 2008/0228106 A1 * | 9/2008 | Forte | A61F 5/4556 600/575 |

(Continued)

FOREIGN PATENT DOCUMENTS

| | | |
|---|---|---|
| CA | 82216 A | 8/1903 |
| CA | 135197 S | 11/2010 |

(Continued)

*Primary Examiner* — Kaylee R Wilson
*Assistant Examiner* — H Q Nguyen
(74) *Attorney, Agent, or Firm* — Gearhart Law, LLC

(57) ABSTRACT

A urine specimen collection apparatus configured to collect a urine specimen from a human user or from an animal is described. The apparatus includes a planar component affixed between a handle portion and a collection portion. The collection portion comprises an outer periphery and an inner periphery, where the inner periphery is defined by an opening. The opening extends through a width of the collection portion and is configured to receive a urine specimen container therein. The handle portion is configured to be gripped by a user during use.

16 Claims, 3 Drawing Sheets

(56) References Cited

U.S. PATENT DOCUMENTS

| | | | | |
|---|---|---|---|---|
| 2009/0076413 A1* | 3/2009 | Robles | ............... | A61B 10/007 |
| | | | | 600/573 |
| 2016/0074018 A1 | 3/2016 | Lependorf | | |
| 2016/0089118 A1* | 3/2016 | Petersilia | ............. | A61B 10/007 |
| | | | | 600/573 |
| 2016/0287163 A1* | 10/2016 | Golden | ............... | A61B 5/1076 |
| 2020/0085455 A1* | 3/2020 | George | ............... | A61B 17/221 |

FOREIGN PATENT DOCUMENTS

| | | | |
|---|---|---|---|
| CA | 141773 S | | 7/2012 |
| WO | WO 9952442 | * | 4/1999 |
| WO | 2009145602 A1 | | 12/2009 |

\* cited by examiner

URINE SPECIMEN COLLECTION APPARATUS

FIELD OF THE EMBODIMENTS

The field of the invention and its embodiments relate to a urine specimen collection apparatus. In particular, the present invention and its embodiments relate to a urine specimen collection apparatus that reduces the inconvenience and discomfort female users experience in the course of providing a urine specimen.

BACKGROUND OF THE EMBODIMENTS

Urinalysis is an essential tool in the healthcare industry, as the urinalysis can provide a range of information concerning the health of a patient. Such information may be useful for medical diagnoses or drug testing purposes. For a female user, the urine specimen is typically collected by the female user sitting on a toilet, bending forward, holding a disposable urine specimen container between her legs, and urinating into the disposable urine specimen container. However, this method is often unhygienic, awkward, and can lead to the female user wetting her hands and/or clothing. Moreover, elderly women or those with medical conditions may be unable to lean forward without losing their balance and thus, losing the collected urine specimen.

Thus, what is needed in the field is a urine specimen collection apparatus that may be used in numerous settings (such as hospitals, healthcare facilities, nursing homes, medical clinics, rehabilitation businesses, hospices, adult daycares, veterinary facilities, etc.) to collect the urine specimen from a human user or from an animal. Additionally, what is needed in the field is a urine specimen collection apparatus that reduces the inconvenience and discomfort female users experience in the course of providing the urine specimen, while allowing female users the ability to hygienically and comfortably provide the necessary urine specimen.

Review of Related Technology

U.S. Pat. No. 7,000,963 B2 describes a holder for grasping and releasing a urine specimen cup. The holder includes: (1) a main frame that has a distal and a proximal portion, (2) a handle integrally formed in the distal frame portion of the main frame, (3) a longitudinally-extending aperture defined within the proximal portion of the main frame, such that the aperture is situated between a pair of opposing and longitudinally-extending side members, (4) an extension member disposed within the aperture of the proximal portion of the main frame, and (5) a specimen cup gripping portion. The (4) extension member has a distal end and a proximal end, where the proximal end is integrally formed as a part of the proximal portion of the main frame, and the extension member is resiliently movable transversely within the aperture and is rotatably movable about its proximal end. The (5) specimen cup gripping portion is cooperatively and integrally formed in the proximal frame portion and in the proximal end of the extension member. A (6) urine specimen cup can be grasped and held within the gripping portion. Also, the (6) urine specimen cup can be released by the gripping portion when the extension member is selectively moved within the main frame aperture.

WO 2009/145602 A1 describes a portable sanitary urine-collector receptacle for male and female use, that includes: a receptacle of a rhomboidal rectangular form. A central part of the receptacle narrows on both sides. The device also includes: a cover that is configured to close over the mouth of the receptacle by pressing the cover against a flange on the circumference of the receptacle, permitting hermetic closure. A holding handle is also provided with the device, such that the user may easily navigate a location of the device during use.

U.S. Pat. No. 5,422,076 A describes an apparatus for sanitarily and easily collecting urine or another liquid specimen for testing. The apparatus includes: a collection vessel and a cover. The collection vessel has a handle portion to assist in the maneuverability of the collection vessel.

U.S. Published Patent Application No. 2002/0179794 A1 describes a disposable female urine sample cup holder for hospital use that enables collection of a urine sample by affixing the urine sample cup holder to a toilet bowl seat.

U.S. Published Patent Application No. 2016/0074018 A1 describes: (i) a clear, measured, tubular specimen collection container; and (ii) a thin retractable/adjustable handle. The handle consists of a telescopic middle stem with an attached twist-on cap at one end and an absorbent, sterile sponge at the other end. For specimen collection, the handle is fully extended to its maximum length and the sponge is placed in the urine stream of a test subject for several seconds. The sponge is then inserted into the specimen collection container, which has a fixed, built-in sieve located in its lower half, with a center slit for urine dipstick testing. The saturated sponge is gently pressed against the sieve to collapse the retractable handle to its shortest length, while the cap is twisted close, sealing the specimen container. The action of twisting the cap to seal the container compresses the sponge against the sieve, causing urine to be expressed into the lower part of the specimen collection container.

U.S. Reissue Pat. No. 33,686 E describes a urine specimen container, combined with a temperature sensitive member, which is capable of signaling a spurious urine specimen when placed in a sufficiently close heat exchange relationship with a urine specimen. The temperature sensitive member contains portions which change color irreversibly at pre-selected temperatures when placed in a sufficiently close heat exchange relationship with the urine specimen. The urine specimen collector itself includes: (1) a bowl-shaped member contoured to fit to close proximity to the body of the user and (2) an integral handle. A (3) cover member is pivotally attached to the handle and functions as a splash guard for the user.

Various urine specimen collection apparatuses exist in the art. However, their means of operation are substantially different from the present disclosure, as the other inventions fail to solve all the problems taught by the present disclosure.

SUMMARY OF THE EMBODIMENTS

The present invention and its embodiments relate to a urine specimen collection apparatus. In particular, the present invention and its embodiments relate to a urine specimen collection apparatus that reduces the inconvenience and discomfort female users experience in the course of providing a urine specimen.

A first embodiment of the present invention describes a urine specimen collection apparatus configured to be used by a human user to collect a urine specimen of a human user or an animal. The urine specimen collection apparatus includes various components, such as: a collection portion, a handle portion, and a planar portion. The planar portion is affixed between the handle portion and the collection portion. The handle portion is configured to be gripped by a user during use. Moreover, the handle portion is configured perpendicular to the planar component.

The collection portion includes an outer periphery and an inner periphery. The inner periphery of the collection portion is defined by an opening. Moreover, the opening may be located in a center of the collection portion. The opening extends through a width of the collection portion and is configured to receive a urine specimen container therein. The urine specimen container is perpendicular to the planar component when received through the opening of the collection portion.

In examples, the collection portion further comprises shaped members cut into or removed from the collection portion. In some examples, each of the shaped members are spaced equidistant from one another. Each of the shaped members begins at the inner periphery and extends in a direction towards the outer periphery of the collection portion. Moreover, the shaped members of the collection portion allow the collection portion to receive differing sized and shaped urine specimen containers.

A second embodiment of the present invention describes a urine specimen collection apparatus configured to collect a urine specimen from a human or an animal. The urine specimen collection apparatus includes numerous components, such as the collection portion, the handle portion, and the planar portion. The planar component is affixed between the handle portion and the collection portion. Moreover, the handle portion is located perpendicular to the planar component and is configured to be gripped by a user during use.

The planar component comprises a length of in a range of approximately 6 inches to approximately 7 inches. The handle portion comprises a length of approximately ¾ of an inch, a width of approximately 6 inches, and a thickness of approximately ¼ of an inch. The collection portion comprises a length in a range of approximately 3 inches to approximately 4 inches.

Moreover, the planar component comprises an inner portion surrounded by an outer perimeter. The inner portion comprises a width of approximately ½ of an inch and the outer perimeter comprises a width of approximately ⅛ of an inch. Additionally, the inner portion of the planar component comprises linear components configured in a design. In some examples, each of the linear components comprises a width of approximately ⅛ of an inch.

The collection portion may comprise a teardrop shape. A pointed portion of the teardrop shape of the collection portion is affixed to the planar component. Moreover, the collection portion may comprise an outer periphery and an inner periphery, where the inner periphery is defined by the opening. The opening may extend through a width of the collection portion and may be configured to receive the urine specimen container therein.

It should be appreciated that the dimensions described herein for the urine specimen collection apparatus and for the components of the urine specimen collection apparatus are for illustrative purposes only and other dimensions are contemplated.

In general, the present invention succeeds in conferring the following benefits and objectives.

It is an object of the present invention to provide a urine specimen collection apparatus that may be used in numerous settings (such as hospitals, healthcare facilities, nursing homes, medical clinics, rehabilitation businesses, hospices, adult daycares, veterinary facilities, etc.) to collect the urine specimen from a human user or from an animal.

It is an object of the present invention to provide a urine specimen collection apparatus that allows for the collection of the urine specimen from a human user or an animal.

It is an object of the present invention to provide a urine specimen collection apparatus that keeps the urine specimen away from hands of a user.

It is an object of the present invention to provide a urine specimen collection apparatus that reduces the inconvenience female users experience in the course of providing a urine specimen.

It is an object of the present invention to provide a urine specimen collection apparatus that reduces the discomfort female users experience in the course of providing a urine specimen.

It is an object of the present invention to provide a urine specimen collection apparatus that allows female users the ability to hygienically and comfortably provide the urine specimen.

DESCRIPTION OF THE PREFERRED EMBODIMENTS

Figure 1:
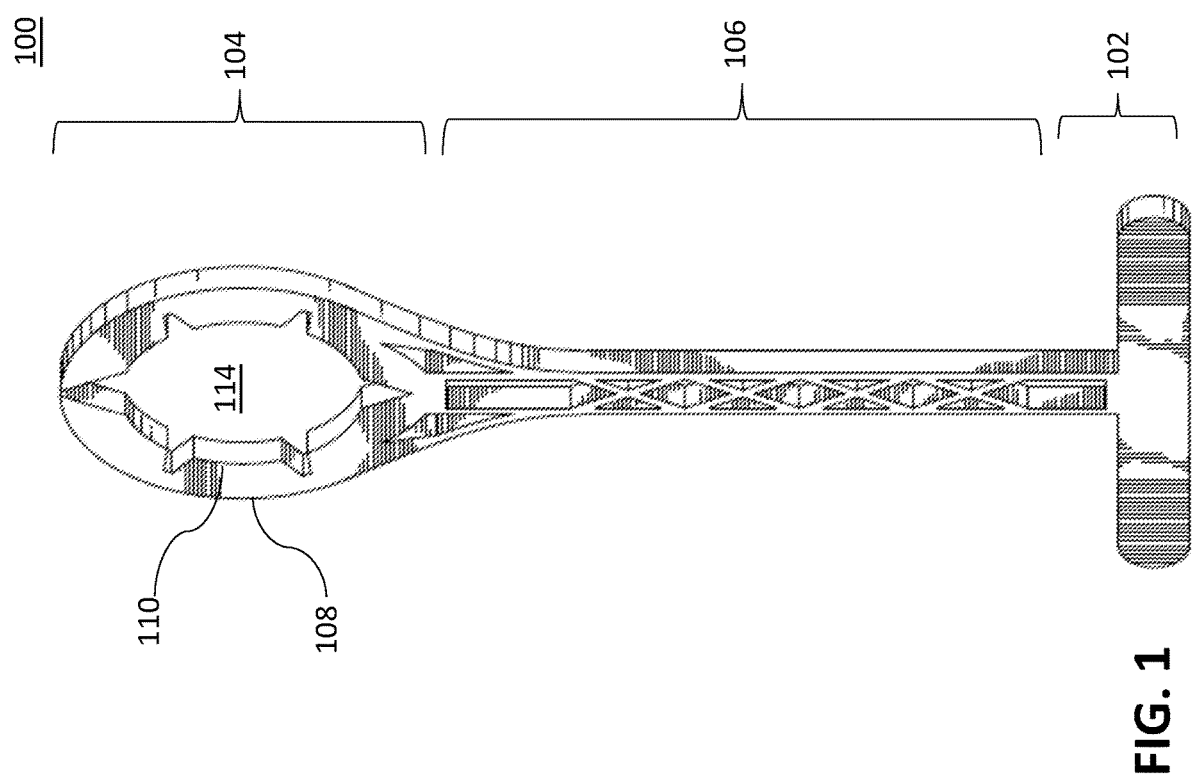
FIG. 1 depicts a perspective view of a urine specimen collection apparatus, in accordance with embodiments of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Figure 2:
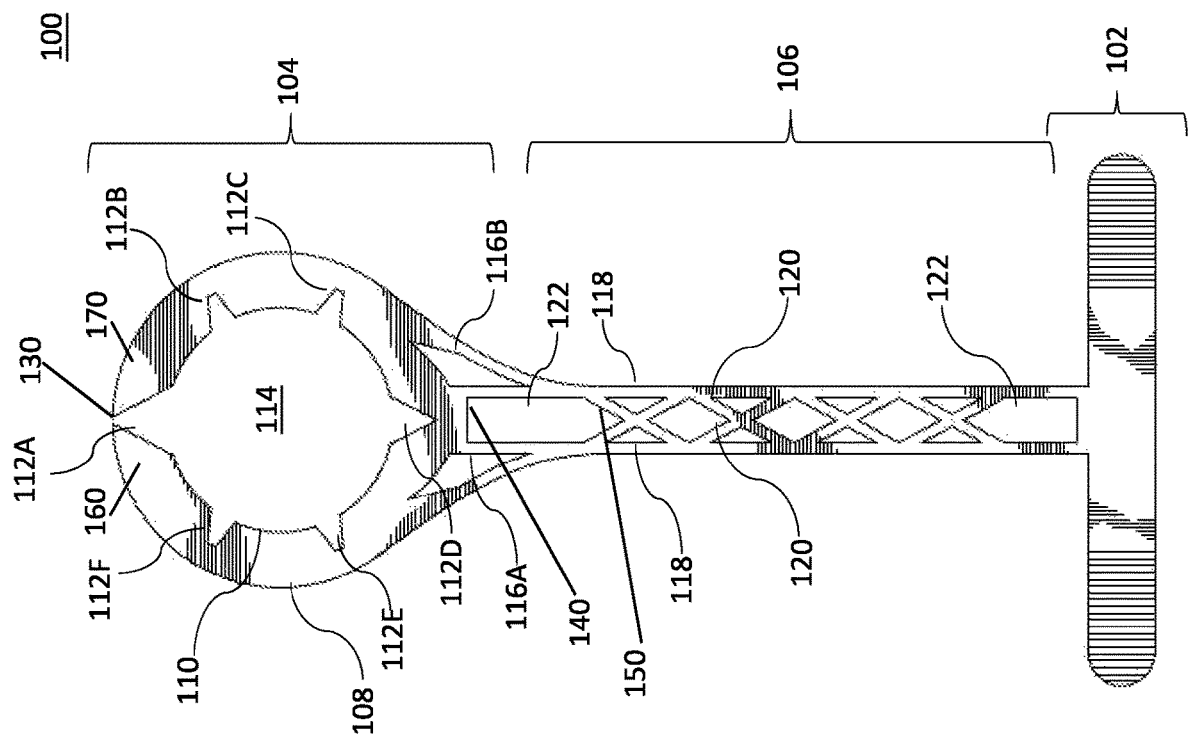
FIG. 2 depicts a front perspective view of a urine specimen collection apparatus, in accordance with embodiments of the present invention.
Figure 3:
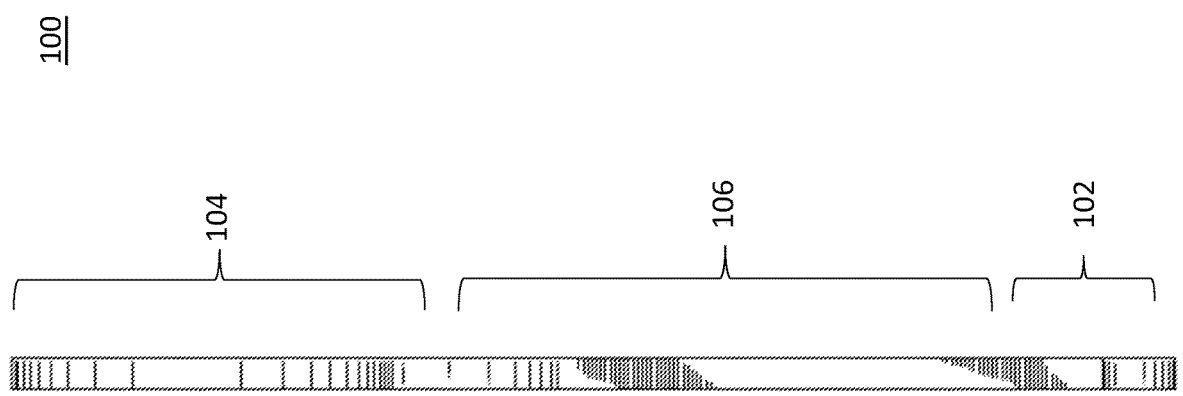
FIG. 3 depicts a side perspective view of a urine specimen collection apparatus, in accordance with embodiments of the present invention.

A urine specimen collection apparatus 100 is depicted in FIG. 1, FIG. 2, and FIG. 3. A human user may utilize the urine specimen collection apparatus 100 to collect a urine specimen from a human or an animal (e.g., for veterinary purposes). The urine specimen collection apparatus 100 includes numerous components, such as: a planar component 106 disposed between a handle portion 102 and a collection portion 104. The planar component 106, the handle portion 102, and the collection portion 104 of the urine specimen collection apparatus 100 are preformed as a singular device. It should be appreciated that the dimensions of the urine specimen collection apparatus 100 and the components of the urine specimen collection apparatus 100 (e.g., the handle portion 102, the collection portion 104, and the planar component 106) described herein are provided for illustrative purposes only and other dimensions are contemplated.

The handle portion 102 is located perpendicular to the planar component 106. In examples, the handle portion 102 comprises a length of approximately ¾ of an inch, a width of approximately 6 inches, and a thickness of approximately ¼ of an inch. Moreover, the handle portion 102 is configured to be gripped by a human user during use when collecting the urine specimen from the human or the animal.

The collection portion 104 of the urine specimen collection apparatus 100 comprises a length in a range of approximately 3 inches to approximately 4 inches. The collection portion 104 additionally comprises a teardrop shape such that a pointed portion of the teardrop shape of the collection portion 104 is affixed to the planar component 106. Moreover, the collection portion 104 comprises an outer periphery 108 and an inner periphery 110. The inner periphery 110 of the collection portion 104 is defined by an opening 114. In examples, the opening 114 is located in a center of the collection portion 104. The opening 114 extends through a width of the collection portion 104, and is configured to receive a urine specimen container (not shown) therein. The urine specimen container (not shown) is used to collect the urine specimen from the human user or from the animal. When the urine specimen container (not shown) is received through the opening 114 of the collection portion 104, the urine specimen container (not shown) is perpendicular to the planar component 106. FIG. 2 shows collection portion 104 having first support structure 160 connected to second support structure 170 at pointed portion of the teardrop shape. The opening 114 of collection portion 104 extends through a width of the collection portion 104, traversing through shaped member 112A at the distal end of collection portion 104 forming gap 130 between first support structure 160 and second support structure 170. The pointed portion of the teardrop shape of collection portion 104 has primary bore 116A and secondary bore 116B. Planar component 106 has inner portion 122 being a recess. First end 140 of the recess of inner portion 122 of planar component 106 separates at least a portion of primary bore 116A from secondary bore 116B. Second end 150 of the recess of inner portion 122 of planar component 106 being tapered.

Additionally, the collection portion 104 further comprises shaped members (e.g., a first member 112A, a second member 112B, a third member 112C, a fourth member 112D, a fifth member 112E, and a sixth member 112F) cut into or removed from the collection portion 104. A quantity of the shaped members is non-limiting and a quantity of six shaped members is provided for illustrative purposes only in FIG. 1 and FIG. 2.

In some examples, each of the shaped members are spaced equidistant from one another. However, in other examples, each of the shaped members may not be spaced equidistant from one another. As depicted in FIG. 1 and FIG. 2, each of the shaped members may be triangular in shape. However, it should be appreciated that the shaped members may comprise any shape. In some examples, each of the shaped members are identical in shape and/or size. In other examples, and as depicted in FIG. 1 and FIG. 2, some of the shaped members are identical in shape and size, such as the second member 112B, the third member 112C, the fourth member 112D, the fifth member 112E, and the sixth member 112F. As depicted in FIG. 1 and FIG. 2, though the first member 112A of the shaped members shares the same shape as the second member 112B, the third member 112C, the fourth member 112D, the fifth member 112E, and the sixth member 112F, the first member 112A has a different size (e.g., is larger) than each of the second member 112B, the third member 112C, the fourth member 112D, the fifth member 112E, and the sixth member 112F.

Moreover, each of the shaped members begins at the inner periphery 110 and extends in a direction towards the outer periphery 108 of the collection portion 104. It should be appreciated that the shaped members of the collection portion 104 allow the collection portion 104 to receive differing sized and shaped urine specimen containers (not shown). For example, the urine specimen container (not shown) may be conical in shape, spherical in shape, square in shape, etc. and may comprise an opening to receive the urine specimen. In other examples, the urine specimen container (not shown) may comprise a cap that is secured to the opening of the urine specimen container (not shown) to securely house the urine specimen within the urine specimen container (not shown).

Further, the planar component 106 of the urine specimen collection apparatus 100 is substantially linear in shape. In some examples, and as depicted in FIG. 1 and FIG. 2, the shape of the planar component 106 is rectangular. However, the shape of the planar component 106 is not limited to such and other shapes are contemplated. The planar component 106 comprises a length in a range of approximately 6 inches to approximately 7 inches. The planar component 106 additionally comprises an inner portion 122 surrounded by an outer perimeter 118. The outer perimeter 118 of the planar component 106 comprises a width of approximately ⅛ of an inch. The inner portion 122 of the planar component 106 comprises a width of approximately ½ of an inch.

Moreover, in examples, inner portion 122 of the planar component 106 comprises linear components 120 configured in a design. As depicted in FIG. 1 and FIG. 2, the linear components 120 are planar in shape and are configured in a repeating "x" design. However, it should be appreciated that the design is not limited to such. In examples, each of the linear components 120 comprises a width of approximately ⅛ of an inch.

For a female user, as explained previously, the urine specimen is typically collected by the female user sitting on a toilet, bending forward, holding a disposable urine specimen container between her legs, and urinating into the disposable urine specimen container. However, this method is often unhygienic and can lead to the female user wetting her hands and/or clothing. Moreover, elderly women or those with medical conditions may be unable to lean forward without losing their balance and thus, losing the collected urine specimen. Thus, the length of the urine specimen collection apparatus 100 being approximately 9 inches to approximately 11 inches allows a female user to collect the urine specimen comfortably without wetting their clothing or hands and additionally minimizes a risk that the female user will fall, which is a specific concern for elderly female users. Additionally, this length may be beneficial for collecting a sample from an uncooperative animal.

The urine specimen collection apparatus 100 and the components of the urine specimen collection apparatus 100 described herein may comprise a wood material and/or a biodegradable polymer material. As such, the urine specimen collection apparatus 100 and the components of the urine specimen collection apparatus 100 are environmentally benign in terms of disposal and use. Moreover, in some examples, the urine specimen collection apparatus 100 may be a one-use device. In some examples, the urine specimen collection apparatus 100 and the components of the urine specimen collection apparatus 100 comprise the same material. In other examples, the urine specimen collection apparatus 100 and the components of the urine specimen collection apparatus 100 comprise differing materials.

The biodegradable polymer material may comprise synthetic or natural polymers. In examples, the biodegradable polymer material may be derived from a petroleum resource, and may include: aliphatic polyesters (e.g., polyglycolide (PGA), polylactide (PLA), poly(lactide-co-glycolide)

(PLGA), polycaprolactone (PCL), poly(butylene succinate) (PBS), poly(p-dioxanone) (PPDO), and/or polycarbonate, etc.), aromatic copolyesters (e.g., poly(butylene adipate-co-terephtalate) (PBAT)), polyamides, poly(ester-amide)s, polyurethanes, and/or polyanhydrides, etc. In other examples, the biodegradable polymer material may be derived from a renewable resource and may include natural polymers or agro-polymers (e.g., proteins) or bacterial polymers (such as microbial polyesters like Poly(hydroxybutyrate) (PHB)). In further examples, the biodegradable polymer material may be a blend of at least two biodegradable polymers. It should be appreciated that the biodegradable polymer material is not limited to any example described herein and other examples are contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A urine specimen collection apparatus configured to hold a urine specimen, the urine specimen collection apparatus comprising:
    a collection portion comprising a first support structure connected to a second support structure, wherein the collection portion having an outer periphery and an inner periphery, the outer periphery of the collection portion forming a teardrop shape, a pointed portion of the teardrop shape of the collection portion has a primary bore and a secondary bore, the primary bare and the secondary bore are integrally formed within the collection portion and not extending beyond the outer periphery of the collection portion, the inner periphery being defined by an opening;
    a shaped member, the shaped member is cut into the collection portion, wherein the shaped member begins at the inner periphery and extends in a direction towards the outer periphery of the collection portion;
    the opening extending through a width of the collection portion, the collection portion is non-continuous, wherein, the opening traversing through the shaped member located at a distal end of the collection portion forming a gap between the first support structure and the second support structure, and being configured to receive a urine specimen container therein;
    a handle comprising a first portion located opposite a second portion configured to be gripped by a user during use, and wherein a width of the first portion and the second portion of the handle is greater than a diameter of the collection portion; and
    a planar component affixed between the handle and the collection portion, the planar component is oriented perpendicular to the first portion and the second portion of the handle portion, the first portion and the second portion of the handle are connected to a distal end of the planar component.

2. The urine specimen collection apparatus of claim 1, wherein the user is a human user, and wherein the urine specimen is urine of the human user.

3. The urine specimen collection apparatus of claim 1, wherein the user is a human user, and wherein the urine specimen is urine of an animal.

4. The urine specimen collection apparatus of claim 1, wherein the collection portion of the urine specimen collection apparatus is configured to hold a urine specimen container perpendicular to a top surface the planar component.

5. The urine specimen collection apparatus of claim 1, wherein the opening is located in a center of the collection portion.

6. The urine specimen collection apparatus of claim 1, wherein the shaped member of the collection portion allows the collection portion to receive differing sized and shaped urine specimen containers.

7. The urine specimen collection apparatus of claim 1, wherein a plurality of shaped members are each spaced equidistant from one another.

8. A urine specimen collection apparatus configured to hold a urine specimen container, the urine specimen collection apparatus comprising:
    a collection portion comprising an outer periphery and an inner periphery, the outer periphery of the collection portion forming a teardrop shape, a pointed portion of the teardrop shape of the collection portion has a primary bore and a secondary bore, the primary bore and the secondary bore arc integrally firmed within the collection portion and not extending beyond the outer periphery of the collection portion, the inner periphery being defined by an opening; the opening extending through a width of the collection portion and having a gap between the inner periphery and the outer periphery, and being configured to receive the urine specimen container therein;
    a handle comprising a first portion located opposite a second portion portion being configured to be gripped by a user during use, and wherein a width of the first portion and the second portion of the handle is greater than a diameter of the collection portion;
    a planar component affixed between the handle portion and the collection portion, the planar component having an inner portion comprising an aperture surrounded by outer perimeter edges, the aperture positioned between the outer perimeter edges of the inner portion of the planar component and traversing the length of the planar component from the handle portion to the collection portion, and wherein the inner portion of the planar component comprises linear support components formed within the aperture in a repeating "x" orientation between the outer perimeter edges of the inner portion, and wherein the planar component is oriented perpendicular to the first portion and the second portion of the handle, the first portion and the second portion of the handle are connected to a distal end of the planar component; and an end of the aperture of the inner portion of the planar component separates at least a portion of the primary bore from the secondary bore.

9. The urine specimen collection apparatus of claim 8, wherein the pointed portion of the teardrop shape of the collection portion is affixed to the planar component.

10. The urine specimen collection apparatus of claim 8, wherein the planar component comprises an inner portion surrounded by an outer perimeter.

11. The urine specimen collection apparatus of claim 10, wherein the outer perimeter comprises a width of ⅛ of an inch.

12. The urine specimen collection apparatus of claim 10, wherein the inner portion comprises a width of ½ of an inch.

13. The urine specimen collection apparatus of claim 8, wherein the collection portion comprises a length in a range of 3 inches to 4 inches.

14. The urine specimen collection apparatus of claim 8, wherein the planar component comprises a length of in a range of 6 inches to 7 inches.

15. The urine specimen collection apparatus of claim 8, wherein the handle portion comprises a length of ¾ of an inch, a width of 6 inches, and a thickness of ¼ of an inch.

16. The urine specimen collection apparatus of claim 8, further comprising a biodegradable polymer being a bacterial polymer.

* * * * *